US008835702B2

(12) United States Patent
Close et al.

(10) Patent No.: US 8,835,702 B2
(45) Date of Patent: Sep. 16, 2014

(54) METHOD FOR MITIGATING THE FORMATION OF BY-PRODUCTS DURING THE PRODUCTION OF HALOALKANE COMPOUNDS

(75) Inventors: Joshua Close, Blasdell, NY (US); Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/481,121

(22) Filed: May 25, 2012

(65) Prior Publication Data

US 2012/0310021 A1 Dec. 6, 2012

Related U.S. Application Data

(60) Provisional application No. 61/492,931, filed on Jun. 3, 2011, provisional application No. 61/492,898, filed on Jun. 3, 2011.

(51) Int. Cl.
| | |
|---|---|
| C07C 17/26 | (2006.01) |
| C07C 17/272 | (2006.01) |
| C07C 17/278 | (2006.01) |
| B01J 35/02 | (2006.01) |
| B01J 31/02 | (2006.01) |
| B01J 38/00 | (2006.01) |
| B01J 23/745 | (2006.01) |
| C07C 17/275 | (2006.01) |
| B01J 23/94 | (2006.01) |
| B01J 37/04 | (2006.01) |

(52) U.S. Cl.
CPC ............. *C07C 17/275* (2013.01); *B01J 35/023* (2013.01); *B01J 31/0257* (2013.01); *B01J 38/00* (2013.01); *B01J 23/745* (2013.01); *B01J 2231/32* (2013.01); *C07C 17/278* (2013.01); *B01J 23/94* (2013.01); *B01J 37/04* (2013.01)
USPC .......................................... 570/237; 570/257

(58) Field of Classification Search
USPC .................................................. 570/171, 261
See application file for complete search history.

(56) References Cited

U.S. PATENT DOCUMENTS

| | | | |
|---|---|---|---|
| 5,902,914 A | 5/1999 | Rygas et al. | |
| 6,187,978 B1 * | 2/2001 | Rygas et al. | 570/257 |
| 6,313,360 B1 * | 11/2001 | Wilson et al. | 570/257 |
| 6,500,995 B1 | 12/2002 | Branam | |
| 6,552,238 B1 * | 4/2003 | Mainz et al. | 570/177 |
| 6,720,466 B2 * | 4/2004 | Wilson et al. | 570/257 |
| 7,094,936 B1 * | 8/2006 | Owens et al. | 570/257 |
| 7,112,709 B2 | 9/2006 | Klausmeyer | |
| 2003/0009066 A1 | 1/2003 | Branam | |
| 2004/0225166 A1 * | 11/2004 | Wilson et al. | 570/171 |
| 2005/0101810 A1 | 5/2005 | Owens et al. | |
| 2008/0091053 A1 | 4/2008 | Tung et al. | |

FOREIGN PATENT DOCUMENTS

| | | |
|---|---|---|
| EP | 0729932 A1 | 9/1996 |
| JP | 2000-086545 A | 3/2000 |
| JP | 2000086545 A * | 3/2000 |

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

Disclosed is a process for the manufacture of haloalkane compounds, and more particularly, an improved process for the manufacture of the compound 1,1,1,3,3-penta-chloropropane (HCC-240fa), which mitigates the formation of by-products from vinyl chloride ($CH_2$=CHCl). The present invention is also useful in the manufacture of other haloalkane compounds such as HCC-250 and HCC-360. One embodiment of the invention comprises a method for mitigating 1,1,3,3,5,5-hexachloropentane and 1,1,1,3,5,5-hexachloropentane formation in the HCC-240fa manufacturing process, in which $FeCl_3$, is introduced to a reactor only after the start-up phase has ended and a continuous operation has started. In a preferred embodiment, "pre-chelated" $FeCl_3$, which is concentrated in a catalyst recovery column, is introduced to reactor after the continuous operation has started.

31 Claims, No Drawings

US 8,835,702 B2

METHOD FOR MITIGATING THE FORMATION OF BY-PRODUCTS DURING THE PRODUCTION OF HALOALKANE COMPOUNDS

CROSS-REFERENCE TO RELATED APPLICATION

This application claims domestic priority to commonly owned, U.S. Provisional Patent Application Ser. No. 61/492,931, filed Jun. 3, 2011, the disclosure of which is hereby incorporated herein by reference.

This application also claims domestic priority to commonly owned, U.S. Provisional Patent Application Ser. No. 61/492,898, filed Jun. 3, 2011, the disclosure of which is hereby incorporated herein by reference.

FIELD OF THE INVENTION

The present invention relates to a process for the manufacture of haloalkane compounds, and more particularly to an improved process for the manufacture of 1,1,1,3,3-pentachloro-propane (HCC-240fa). The present invention is also useful in the manufacture of other haloalkane compounds such as HCC-250 and HCC-360.

BACKGROUND OF THE INVENTION

The compound 1,1,1,3,3-pentachloropropane (HCC-240fa) is a raw material for producing 1,1,1,3,3-pentafluoro-propane (HFC-245fa), which is a non-ozone depleting chemical and can be used as blowing agent, energy transfer medium, and so on. Addition reactions for preparing useful haloalkanes, such as HCC-240fa, are known in the art. For example, U.S. Pat. No. 6,313,360 teaches a process for producing HCC-240fa by reacting carbon tetrachloride ($CCl_4$) and vinyl chloride (VCM) in the presence of a catalyst mixture comprising organophosphate, e.g., tributylphosphate (TBP), metallic iron and ferric chloride under conditions sufficient to produce a product mixture containing HCC-240fa. The 240fa product is then recovered by separating it from reactants, catalyst and by-products. See also, U.S. Pat. Nos. 5,902,914, 6,187,978, 6,500,995, 6,552,238, 6,720,466, 7,112,709, and U.S. Patent Publication No. 2008/0091053. The disclosures of all of these references are hereby incorporated herein by reference.

Applicants have unexpectedly discovered that when using the catalyst mixture disclosed in U.S. Pat. No. 6,313,360, namely, TBP, metallic iron, and ferric chloride, substantial amounts of $CCl_4$ originating by-products such as hexachloroethane, tetrachloroethene, chloroform, and hexachlorobutadiene are generated during the reaction of $CCl_4$ and VCM, especially during the start-up of the reaction. The formation of these by-products causes a significant decrease in the HCC-240fa selectivity.

Therefore, the present inventors have come to appreciate the need for an improved start-up process for the manufacture of HCC-240fa. Embodiments of the present invention solve this problem.

Applicants have also discovered that after the initial start-up described above, e.g., when this reaction is conducted as a batch or preferably, as a continuous operation, the reactor eventually contains a concentrated amount of HCC-240fa, e.g., having a composition of potentially greater than 60 wt % of the reactor organic content. Under these circumstances, when fresh catalyst consisting of iron powder ($Fe^0$) and tributylphosphate (TBP), is introduced into the reactor, the VCM preferentially reacts with the HCC-240fa, instead of the $CCl_4$ to form undesirable by-products such as 1,1,3,3,5,5-hexachloro-pentane (major) and 1,1,1,3,5,5-hexachloropentane (minor). For convenience purpose, these hexachloropentanes are called vinyl chloride originating by-products. Depending on the TBP concentration, the selectivity to 1,1,3,3,5,5-hexachloropentane can reach 65%, which causes a substantial yield loss of the desired HCC-240fa product.

Therefore, the present inventors have come to appreciate a need for means by which the formation of these vinyl chloride originating by-products can be avoided during this process. Embodiments of this invention also provide a solution to this problem.

SUMMARY OF THE INVENTION

The present invention thus relates to improved processes for the manufacture of haloalkane compounds, and more particularly, to an improved process for the manufacture of the compound 1,1,1,3,3-pentachloropropane (HCC-240fa). The present invention is also useful in the manufacturing processes for other haloalkane compounds such as HCC-250 and HCC-360.

In certain embodiments, improvements to the process for the manufacture HCC-240fa include modifications made to the start-up reaction, which is typically a batch reaction, wherein by-products from $CCl_4$ are reduced by appropriate selection of catalysts. Specifically, it has been found that $FeCl_3$ should be minimized or completely omitted during the start-up phase of the reaction.

In certain embodiments, improvements to the process for the manufacture HCC-240fa include modifications made to the post start-up reaction, i.e., after the formation of HCC-240fa has begun, and has reached a reactive or high level in the reactor. The high level of HCC-240fa in the reactor organic content can vary, but is typically at least about 35%, or 45%, or 55%, or 65%, or higher. At these high levels, the HCC-240fa can react with VCM instead of with $CCl_4$, causing undesirable by-products and loss of the desired product. This stage of the reaction, which can be conducted batchwise or continuously, includes a reduction of by-product formation by another appropriate selection of catalysts. Specifically, in this part of the reaction, the use of $FeCl_3$ as a catalyst is very desirable, as it suppresses the formation of undesirable vinyl chloride originating by-products.

In one embodiment, the present invention is directed to an improved process for making HCC-240fa. This aspect of the invention can be generally described as a method for mitigating vinyl chloride originating by-products, particularly 1,1,3,3,5,5-hexachloro-pentane formation in the HCC-240fa manufacturing process, in which $FeCl_3$ is introduced to reactor only after the start-up batch phase has been conducted, and preferably once a continuous operation has been started.

$FeCl_3$, when added to the reactor, becomes chelated, in situ, with tributyl-phosphate (or with another organophosphate) present in the reactor. If neat or untreated $FeCl_3$ is chelated in the reactor, the $FeCl_3$ is referred to herein as chelated $FeCl_3$. Another way in which $FeCl_3$ can be added to the reactor is to concentrate pre-chelated $FeCl_3$ included in reactor effluent stream, and recycle it back to the reactor. Pre-chelated $FeCl_3$ is a preferred catalyst herein.

Applicants have unexpectedly found that in the presence of ferric chloride (chelated or pre-chelated), the formation of the undesired by-product 1,1,3,3,5,5-hexa-chloropentane is greatly suppressed to about 5% or less. Accordingly, in the present invention, $FeCl_3$, or more preferably, "pre-chelated" $FeCl_3$, generated in a prior reaction, is introduced to the processing reactor to prevent or reduce the formation of the undesired vinyl chloride originating by-products, 1,1,3,3,5,5-hexachloro-pentane and 1,1,1,3,5,5-hexachloro-pentane.

The present invention is also useful in the manufacturing processes for other haloalkane compounds such as HCC-250 and HCC-360:

(1) HCC-250 may be made from $CCl_4$ and ethylene as per the following reaction:

$$CCl_4 + CH_2 = CH_2 \rightarrow CCl_3CH_2CH_2Cl$$

In this case, the undesired by-products which are reduced or eliminated by the processing conditions taught herein are $CCl_3CH_2CH_2CH_2CH_2Cl$ and $ClCH_2CH_2CCl_2CH_2CH_2Cl$.

(2) HCC-360 may be made from $CCl_4$ and 2-chloropropene as per the following reaction:

$$CCl_4 + CH_2 = CClCH_3 \rightarrow CCl_3CH_2CCl_2CH_3$$

In this case, the undesired byproducts which are reduced or eliminated by the processing conditions taught herein are $CCl_3CH_2CCl(CH_2CCl_2CH_3)CH_3$ and $CH_3CCl_2CH_2CCl_2CH_2CCl_2CH_3$.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

Start-Up Reaction

In certain embodiments, the reaction is carried out in a glass-lined reactor, which is equipped with an agitator. In one embodiment of the present invention, the reaction of vinyl chloride and carbon tetrachloride to form HCC-240fa is initiated utilizing only iron $Fe^0$ powder as the catalyst and an organophosphate compound such as tributylphosphate (TBP) as the co-catalyst, and omitting the use of ferric chloride.

The iron powder useful in this invention is preferably a fine powder of pure metallic iron, preferably with a particle size smaller than 325 mesh. Iron powder may be added to the reactor by any means, but powder slurry in carbon tetrachloride, in TBP, or in the mixture of both is preferred. While iron powder is preferred, any iron object can be used, such as iron balls, iron wire, iron shavings, and the like.

The co-catalyst TBP is a chelating agent and also serves as solvent to help dissolve the solid catalyst. The mole ratio of iron powder to tributylphosphate may be about 0.05:1 to about 500.0:1, preferably about 1.0:1 to about 100.0:1, and more preferably about 1.5:1 to about 10:1. The preferred concentration of the catalyst in the reaction mixture is from about 0.001 to about 20 weight percent, preferably from about 0.01 to about 10 weight percent, and more preferably from about 0.1 to about 5 weight percent. Generally, the mole ratio of $CCl_4$ to VCM is from about 0.02:1 to about 50:1. Preferably, the ratio is from about 0.1:1 to about 4.0:1 and more preferably from about 1:1 to about 3:1.

Additional organophosphate co-catalysts useful herein are the following: triphenylphosphate, tributylphosphate, trimethylphosphate, triethylphosphate, tripropylphosphate or any similar organophosphate compound, and mixtures of two or more of these.

In a batch start-up process, a certain amount of $CCl_4$ is first charged to a pre-purged (with an inert gas such as nitrogen) reactor followed by a slurry mixture of iron powder, TBP, and $CCl_4$. The reactor is then heated to a temperature of from about 40° C. to about 180° C., preferably from about 85° C. to about 150° C., with agitation. VCM is then fed into the reactor as a vapor until the consumption of vinyl chloride by the carbon tetrachloride in the reactor batch is equivalent to the target molar ratio.

In a preferred embodiment, the initial feed of vinyl chloride will be introduced without the use of a flow control mechanism (e.g., RCV, needle valve, etc.) in an effort to maximize the initial feed rate. The reaction temperature and catalytic activity inherently determine the reactor pressure, which is preferably from 30 psia to 60 psia. The batch reaction is preferably carried out until a VCM conversion of higher than 95% is achieved. In certain embodiments, the operation is then transited into a continuous operational mode.

Continuous Operation

In a continuous operation, $CCl_4$ and VCM are continuously fed into the reactor at desired ratio. In the inventive process, $FeCl_3$, iron powder and TBP can be added into reactor periodically or continuously, but the continuous mode is preferred. Any form of $FeCl_3$ can be used. Non-limiting examples include solid $FeCl_3$, and $FeCl_3$ solution, and $FeCl_3$ suspension. Non-limiting examples of solvents that can be used to make $FeCl_3$ solutions or suspensions include $CCl_4$, TBP, HCC-240fa, and isomers of hexachloro-pentane.

The reaction is preferably carried out at a residence time of from about 0.01 hours to about 24 hours, preferably from about 1 hour to about 12 hours. The reaction conditions are selected for high VCM efficiency, high HCC-240fa yield, and low by-products production. Table 1 lists selected reaction conditions.

TABLE 1

| Condition | Range | Preferred range |
| --- | --- | --- |
| Reactor temperature (° C.) | 40° C. to 180° C. | 85° C. to 150° C. |
| Reactor pressure (psia) | 14 psia to 200 psia | 30 psia to 120 psia |
| $CCl_4$/VCM (mol/mol) | 0.02:1 to 50:1 | 1:1 to 3:1 |
| Fe/VCM (mol/mol) | 0 to 500:1 | 0.01:1 to 100:1 |
| TBP/VCM (mol/mol) | 0 to 1:1 | 0.001:1 to 0.1:1 |
| $FeCl_3$/VCM (mol/mol) | 0 to 1:1 | 0.001:1 to 0.033:1 |

In a continuous operation, the reactor contents are continually drawn through a tube immersed into liquid. After going through a filter where iron particles are trapped, the reactor effluent stream is flash-distilled to remove a "top" stream including unreacted $CCl_4$ and VCM (if any) feed materials and the HCC-240 reaction product, while the catalyst/co-catalyst mixture remains. The distillation may be performed in one or more distillation columns, which are well known in the art.

Preferably, the flash-distillation is conducted in two steps: first, flash-distillation is conducted at a temperature less than the reaction temperature under a pressure, preferably under vacuum, to remove any unreacted $CCl_4$ and/or VCM, followed by another vacuum flash-distillation at a lower pressure to remove the HCC-240fa reaction product. The "bottoms" stream contains ferric chloride, TBP, HCC-240, isomers of hexachloropentane, and possibly other high boiling components.

In a preferred embodiment of the present invention, the "bottom" stream which includes pre-chelated $FeCl_3$ is recycled back to the reactor. The pre-chelated $FeCl_3$ included in the stream functions to suppress the formation of 1,1,3,3,5,5-hexachloro-pentane, much in the same way as neat or fresh $FeCl_3$ does when introduced as discussed above.

The distilled, unreacted $CCl_4$ and VCM may be recycled back to the reactor. Periodical purges may be applied to avoid accumulation of heavy by-products such as hexachloropentane isomers in the catalyst recycle stream.

In a later step of the process, the present invention provides for the purification of the crude product by distillation. Fractional vacuum distillation is carried out at about 5 to about 200 mm Hg and a temperature of about 50° C. to about 150° C. to recover the product. It has been discovered that when this purification step is carried out in the presence of an organophosphate compound such as tributylphosphate or other metal chelating compound, the distillation yield of purified product is significantly improved.

While not wishing to be bound by any particular theory, it is believed that the tributylphosphate acts to prevent the decomposition of the HCC-240fa product. Thus, in a preferred embodiment, the purification step includes the addition of an amount of a metal chelating compound sufficient to improve the HCC-240fa product yield. Preferably, 5 weight percent of tributylphosphate is used.

If desired, the iron catalysts used in the production of the haloalkane compounds herein may be captured and recycled by the use of an electromagnetic separation unit (EMSU). When energized, the EMSU functions to remove the iron particles from the reactor effluent; when de-energized, the iron particles captured by the EMSU can be flushed back into the reactor for re-use in the continued production of the desired haloalkane compounds, such as HCC-240fa.

The following non-limiting examples serve to further illustrate the present invention.

Example 1

241 g iron powder, 70 g of ferric chloride, and 346 g of tributylphosphate were mixed batchwise in a nitrogen purged, 5 gallon, glass lined, jacketed reactor containing 15.1 lbs of carbon tetrachloride. Using low pressure steam, the mixture was brought to a temperature of 90° C., venting non-condensables during warm-up. At temperature, 4.1 lbs of vinyl chloride was introduced into the reactor and was allowed to be consumed over a period of about 1 day. Samples were retrieved from the reactor at the conclusion of the reaction and were analyzed with GC. GC results suggest that the reactor selectivity to HCC-240fa was 76%. Carbon tetrachloride by-products including hexachloroethane, tetrachloroethene, chloroform, and hexachlorobutadiene make up a sum total of 12% of the total reactor selectivity.

Example 2

In a 150 cc, pressure rated test tube, 2.53 g tributylphosphate, 0.51 g ferric chloride, and 1.8 g of iron powder were mixed with 50 g carbon tetrachloride. The vessel was submerged in a hot oil bath that was heated to 90° C. The chemical were continuously stirred at temperature for 4 hours. After the mixing time elapsed, the test tube was removed from the oil bath and cooled back to room temperature. Samples were taken and analyzed with GC. GC analysis revealed the presence of carbon tetrachloride originating by-products which include hexachloroethane, tetrachloroethene, chloroform, and hexachlorobutadiene. This reaction occurred in the absence of vinyl chloride.

Example 3

Similar to Example 2, in a 150 cc, pressure rated test tube, 2.53 g tributyl-phosphate and 1.8 g of iron powder were mixed with 50 g carbon tetrachloride, omitting the addition of ferric chloride. Again, the vessel was submerged in a hot oil bath that was heated to 90° C. for 4 hours. The mixture was cooled to room temperature and samples were retrieved for GC analysis. Data showed no indication of a reaction as there were no by-products formed.

Example 4

Omitting ferric chloride addition, 136 g tributylphosphate and 300 g of iron powder (mesh 325) were added to 41 lbs of carbon tetrachloride in a nitrogen purged, 5 gallon, glass lined, jacketed reactor. Using low pressure steam, the mixture was brought to a temperature of 100° C., venting non-condensables during warm-up. At temperature, vapor vinyl chloride was injected into the liquid mixture utilizing the reactor dip pipe. During vinyl chloride addition, the feed was allowed to flow with no external control (control valve).

The reaction was allowed proceed until 8.3 lbs of vinyl chloride was added to the reactor. Following the reaction, a sample was retrieved and analyzed with GC. Results showed that overall reactor selectivity to HCC-240fa was 90.7%, with 4.9% consisting of the sum of by-products containing hexachloroethane, tetrachloroethene, chloroform, and hexachlorobutadiene.

Example 5

Following similar practices to conditions disclosed in Example 3, 136 g tributylphosphate and 300 g of iron powder (mesh 325) were added to 41 lbs of carbon tetrachloride in a nitrogen purged, 5 gallon, glass lined, jacketed reactor, again omitting ferric chloride. Again the reactor was heated to 100° C. and vented during warm-up. However, at temperature, vapor vinyl chloride was introduced into the liquid mixture in the reactor at a controlled rate using a pneumatically driven research control valve.

The reaction was allowed proceed until 8.3 lbs of vinyl chloride was added to the reactor. Following the reaction, a sample was retrieved and analyzed with GC. Results showed that overall reactor selectivity to HCC-240fa was reduced to 85.3%, with 10.8% consisting of the sum of hexachloroethane, tetrachloroethene, chloroform, and hexachlorobutadiene.

Example 6

In a 150 cc pressure rated test tube reactor, 24.5 g of 1,1,1,3,3-pentachloro-propane, 10.5 g carbon tetrachloride, 0.35 g tributylphosphate, and 1.23 g iron powder (325 mesh) were mixed and purged with nitrogen. The test tube was immersed in a hot oil bath and preheated to 90° C. At temperature, vapor vinyl chloride was introduced into the test tube reactor. Upon the addition of vinyl chloride, the temperature of the bath was raised to 100° C. Once a period of 5 hours had elapsed, the reaction was cooled and a sample of the liquid media was retrieved for GC analysis. This analysis showed that the selectivity of 1,1,3,3,5,5-hexachloropentane was 28.8%. The source cylinder of vinyl chloride indicated that 13.5 g of material was introduced over the duration of the experiment.

Example 7

Similar to Example 6, 24.5 g of 1,1,1,3,3-pentachloropropane, 10.5 g carbon tetrachloride, 0.35 g tributylphosphate, 0.07 g of ferric chloride, and 1.23 g iron powder (325 mesh) were mixed in a 150 cc pressure rated test tube reactor that was purged with nitrogen. Again, the test tube was immersed in a hot oil bath and preheated to 90° C. At temperature, vapor vinyl chloride was introduced into the test tube reactor and the temperature re-raised to 100° C. Once a period of 5 hours had elapsed, the reaction was cooled and a sample of the liquid media was retrieved for GC analysis. This analysis showed that the selectivity of 1,1,3,3,5,5-hexachloropentane was 7.9%. 5.6 g of vinyl chloride were introduced into the reactor.

Example 8

Instead of using neat tributylphosphate and ferric chloride as shown in Example 7, 24.5 g of 1,1,1,3,3-pentachloropropane, 10.5 g carbon tetrachloride, 1.08 g of retrieved bottoms product from a catalyst recovery column, composed of 17 wt % tributyl-phosphate and 1.23 g iron powder (325 mesh) were mixed in a 150 cc pressure rated test tube reactor that was purged with nitrogen. The test tube was immersed in a hot oil bath and preheated to 90° C. At temperature, vapor vinyl chloride was introduced into the test tube reactor and the temperature re-raised to 100° C. After 5 hours had elapsed, the reaction was cooled and a sample of the liquid media was retrieved for GC analysis. This analysis showed that the selectivity of 1,1,3,3,5,5-hexachloropentane was 3.1%. 6.4 g of vinyl chloride were introduced into the reactor.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the manufacture of haloalkane compounds consisting essentially of reacting carbon tetrachloride and an alkene wherein $CCl_4$ originating by-products are minimized during the start-up phase of the reaction comprising the step of conducting the reaction with only an iron metal catalyst and one or more organophosphate compounds as a co-catalyst;
wherein the alkene is selected from the group consisting of vinyl chloride, ethylene and 2-chloropropene;
wherein the haloalkane compounds are selected from the group consisting of HCC-240fa, HCC-250 and HCC-360;
wherein the $CCl_4$ byproducts being minimized include hexachloroethane, tetrachloroethene, chloroform, and hexachlorobutadiene, normally generated during the reaction of $CCl_4$ and the alkene; and wherein once the reaction contains at least about 35 wt % of the haloalkane compound, further including a step in which $FeCl_3$ is introduced to the reactor to prevent the formation of undesirable by-products including 1,1,3,3,5,5-hexachloropentane and 1,1,1,3,5,5-hexachloropentane.

2. The process of claim 1, wherein the iron catalyst has a form selected from the group consisting of iron powder, iron balls, iron wire, iron shavings, and mixtures thereof.

3. The process of claim 1, wherein the organophosphate co-catalyst is selected from the group consisting of tributylphosphate, trimethylphosphate, triethylphosphate, tripropylphosphate, triphenylphosphate and mixtures of two or more of these.

4. The process of claim 1, which is conducted as a continuous operation.

5. The process of claim 1, which is conducted as a batch operation.

6. A process for manufacturing 1,1,1,3,3-pentachloropropane, which consists essentially of:
(a) producing a product mixture by reacting carbon tetrachloride and vinyl chloride in the presence of a catalyst mixture consisting of iron metal and tributylphosphate under conditions sufficient to produce HCC-240fa while minimizing the formation of $CCl_4$ originating by-products,
(b) once the reaction in step (a) contains at least about 35 wt % of HCC-240fa, continuing the process by producing a product stream in a continuous operation by reacting carbon tetrachloride and vinyl chloride in the presence of a catalyst mixture consisting essentially of iron metal, $FeCl_3$, and tributylphosphate under conditions sufficient to produce HCC-240fa while minimizing the formation of vinyl chloride originating by-products, and
(c) recovering HCC-240fa from said product stream of step (b).

7. The process of claim 6, wherein the mole ratio of iron metal to tributylphosphate ranges from about 0.05:1 to about 500:1.

8. The process of claim 6, wherein the mole ratio of iron metal to tributylphosphate ranges from about 10:1 to about 100:1.

9. The process of claim 6, wherein the mole ratio of iron metal to tributylphosphate ranges from about 1.5:1 to about 10:1.

10. The process of claim 6, wherein the concentration of the catalyst in the reaction mixture ranges from about 0.001 to about 20 weight percent.

11. The process of claim 6, wherein the concentration of the catalyst in the reaction mixture ranges from about 0.01 to about 10 weight percent.

12. The process of claim 6, wherein the concentration of the catalyst in the reaction mixture ranges from about 0.1 to about 5 weight percent.

13. The process of claim 6, wherein the mole ratio of $CCl_4$ to VCM ranges from about 0.02:1 to about 50:1.

14. The process of claim 6, wherein the mole ratio of $CCl_4$ to VCM ranges from about 0.1:1 to about 4:1.

15. The process of claim 6, wherein the mole ratio of $CCl_4$ to VCM ranges from about 1:1 to about 3:1.

16. The process of claim 6, wherein step (c) further comprises the steps of removing the iron metal from the catalyst mixture, followed by the flash-distilling of the HCC-240fa product stream to separate the HCC-240fa, unreacted $CCl_4$ and unreacted VCM from catalyst mixture, and recycling the remaining catalyst components to step (a).

17. The process of claim 6, wherein the iron catalyst has a form selected from the group consisting of iron powder, iron balls, iron wire, iron shavings, and mixtures thereof.

18. The process of claim 17, wherein the iron powder comprises a fine powder of pure metallic iron.

19. The process of claim 18, wherein the iron powder has a particle size smaller than 325 mesh.

20. The process of claim 18, wherein the iron powder is added to the reactor by powder slurry in carbon tetrachloride.

21. The process of claim 18, wherein the iron powder is added to the reactor by powder slurry in TBP.

22. The process of claim 18, wherein the iron powder is added to the reactor by powder slurry in a mixture of $CCl_4$ and tributylphosphate.

23. The process of claim 6, wherein the organophosphate co-catalyst is selected from the group consisting of tributylphosphate, trimethylphosphate, triethylphosphate, tripropylphosphate, triphenylphosphate, and mixtures of two or more of these.

24. The process of claim 6, wherein step (a) is conducted as a batch operation, and step (b) is conducted as a continuous operation which includes the use of $FeCl_3$.

25. The process of claim 24, wherein the $FeCl_3$ is selected from the group consisting of solid $FeCl_3$, a solution of $FeCl_3$, and a suspension of $FeCl_3$.

26. The process of claim 24, wherein the $FeCl_3$ comprises pre-chelated $FeCl_3$.

27. A process for the manufacture of haloalkane compounds from carbon tetrachloride and an alkene consisting of the steps of:

(a) reacting $CCl_4$ with an alkene in the presence of an iron metal catalyst and one or more organophosphate compounds as a co-catalyst; and (b) once the reaction in step (a) contains at least about 40 wt % of the haloalkane, continuing the process by reacting $CCl_4$ with an alkene in the presence of $FeCl_3$ and iron metal as a catalyst system and one or more organophosphate compounds as a co-catalyst.

28. A process for the manufacture of haloalkane compounds consisting essentially of reacting carbon tetrachloride and an alkene wherein $CCl_4$ originating by-products are minimized during the start-up phase of the reaction including the step of starting the reaction with only an iron metal catalyst and one or more organophosphate compounds as a co-catalyst;

wherein the alkene is selected from the group consisting of vinyl chloride, ethylene and 2-chloropropene;

wherein the haloalkane compounds are selected from the group consisting of HCC-240fa, HCC-250 and HCC-360; and wherein once initial the reaction contains greater than about 50 wt % of haloalkane, the reaction further including a step in which $FeCl_3$ is introduced to the reactor, such that the formation of the undesired by-product 1,1,3,3,5,5-hexachloropentane is suppressed to about 5% or less.

29. The process of claim 28, wherein the haloalkane is HCC-240fa.

30. The process of claim 28, wherein the haloalkane is HCC-250.

31. The process of claim 28, wherein the haloalkane is HCC-360.

* * * * *